(12) United States Patent
Ryu et al.

(10) Patent No.: US 9,260,447 B2
(45) Date of Patent: Feb. 16, 2016

(54) METHOD FOR PREPARING HIGH-PURITY ANHYDROSUGAR ALCOHOL HAVING IMPROVED YIELD BY USING WASTE FROM CRYSTALLIZATION STEP

(71) Applicant: SAMYANG GENEX CORPORATION, Seoul (KR)

(72) Inventors: Hoon Ryu, Daejeon (KR); Young Jae Jung, Daejeon (KR); Jin Kyung Kim, Daejeon (KR); Do Hyun Kyung, Daejeon (KR); Hyuk Min Park, Incheon (KR); Seong Ho Cho, Seoul (KR)

(73) Assignee: SAMYANG GENEX CORPORATION, Seoul (KR)

( * ) Notice: Subject to any disclaimer, the term of this patent is extended or adjusted under 35 U.S.C. 154(b) by 0 days.

(21) Appl. No.: 14/441,444

(22) PCT Filed: Nov. 6, 2013

(86) PCT No.: PCT/KR2013/009998
§ 371 (c)(1),
(2) Date: May 7, 2015

(87) PCT Pub. No.: WO2014/073848
PCT Pub. Date: May 15, 2014

(65) Prior Publication Data
US 2015/0252054 A1    Sep. 10, 2015

(30) Foreign Application Priority Data
Nov. 8, 2012    (KR) .................. 10-2012-0126082

(51) Int. Cl.
*C07D 493/04* (2006.01)
*B01J 19/24* (2006.01)
*C07C 29/80* (2006.01)
*C07C 29/94* (2006.01)
*C07C 31/26* (2006.01)

(52) U.S. Cl.
CPC .............. *C07D 493/04* (2013.01); *B01J 19/24* (2013.01); *C07C 29/80* (2013.01); *C07C 29/94* (2013.01); *C07C 31/26* (2013.01)

(58) Field of Classification Search
CPC ...................................................... C07D 493/04
USPC ............................................................. 549/464
See application file for complete search history.

(56) References Cited

U.S. PATENT DOCUMENTS

| 4,564,692 A | 1/1986 | Feldmann et al. |
| 6,639,067 B1 | 10/2003 | Brinegar et al. |
| 2004/0110969 A1 | 6/2004 | Fleche et al. |

FOREIGN PATENT DOCUMENTS

| KR | 10-2001-0079763 A | 8/2001 |
| KR | 10-2003-0007926 A | 1/2003 |
| KR | 10-1079518 B1 | 10/2011 |
| KR | 10-2012-0066904 A | 6/2012 |
| WO | WO 00/41985 A1 | 7/2000 |
| WO | WO 03/089420 A2 | 10/2003 |

OTHER PUBLICATIONS

International Search Report issued in PCT/KR2013/009998, mailed on Feb. 26, 2014.

*Primary Examiner* — Taofiq A Solola
(74) *Attorney, Agent, or Firm* — Birch, Stewart, Kolasch & Birch, LLP

(57) ABSTRACT

The present invention relates to a technique for preparing an anhydrosugar alcohol using hydrogenated sugar as a raw material and, more specifically, to a technique for preparing a high-purity anhydrosugar alcohol by adding an acid to hydrogenated sugar (for example, hexitol) to convert same to an anhydrosugar alcohol, then distilling the converted liquid, and crystallizing the distilled liquid in a solvent, the technique removing a crystallization solvent from a crystallization mother liquor generated during a crystallization step and then introducing the resultant product together with the distilled liquid and the converted liquid into a distillation step, thereby being capable of improving the total distillation yield of the anhydrosugar alcohol, improving distillation efficiency by improving the mobility of a distillate, and further reducing the amount of generated waste and treatment costs and thus highly efficiently preparing the high-purity anhydrosugar alcohol at reduced costs.

11 Claims, 1 Drawing Sheet

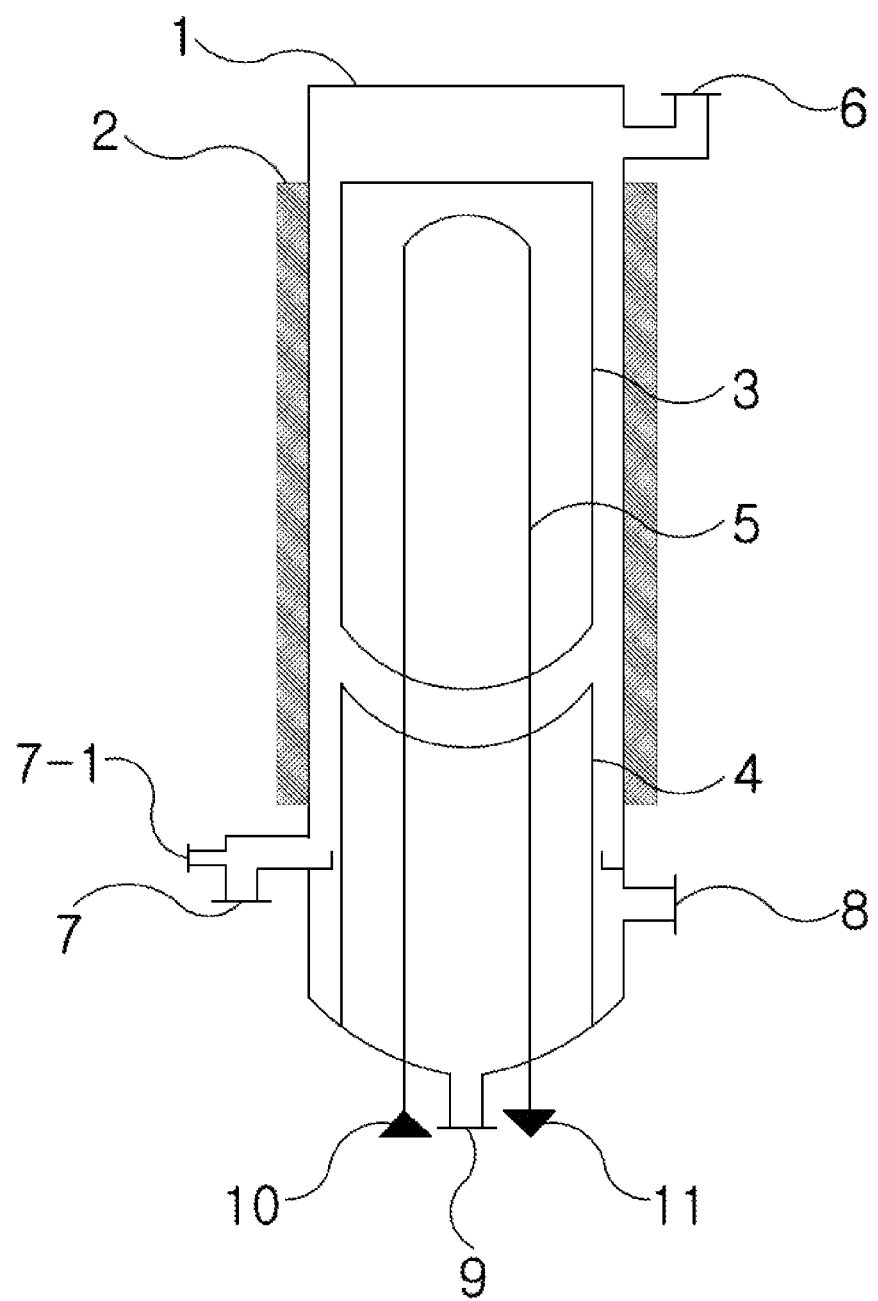

METHOD FOR PREPARING HIGH-PURITY ANHYDROSUGAR ALCOHOL HAVING IMPROVED YIELD BY USING WASTE FROM CRYSTALLIZATION STEP

TECHNICAL FIELD

The present invention relates to a technology for producing anhydrosugar alcohol by using hydrogenated sugar as raw material, and more specifically a method for producing anhydrosugar alcohol by converting hydrogenated sugar (e.g., hexitol) to anhydrosugar alcohol by addition of an acid thereto, distilling the resulting liquid of the conversion reaction and crystallizing the resulting distillate in a solvent, wherein the solvent for crystallization is removed from the mother liquor generated from the crystallization step and the resulting product is fed to the distillation step together with a distillate and a resulting liquid of the conversion reaction, by which the overall yield of anhydrosugar alcohol can be improved, the distillation efficiency can be increased by improving the flowability of the distillate, and the amount of waste and cost for waste disposal can be reduced, resulting in the production of highly pure anhydrosugar alcohol with low cost and high efficiency.

BACKGROUND ART

Hydrogenated sugar (also referred to as "sugar alcohol") means a compound obtained by adding hydrogen to the reductive end group in sugar, and generally has a chemical formula of $HOCH_2(CHOH)_nCH_2OH$ wherein n is an integer of 2 to 5. According to the carbon number, hydrogenated sugar is classified into tetritol, pentitol, hexitol and heptitol (4, 5, 6 and 7 carbons, respectively). Among them, hexitol having 6 carbons includes sorbitol, mannitol, iditol, galactitol, etc. and in particular, sorbitol and mannitol are very useful materials.

Anhydrosugar alcohol has a diol form with two hydroxyl groups in the molecule, and can be produced by using hexitol derived from starch (for example, Korean Patent No. 10-1079518 and Korean Laid-open Patent Publication No. 10-2012-0066904). Because anhydrosugar alcohol is an environmentally friendly material derived from recyclable natural resources, it has received much interest for a long time and researches on its production continue to proceed. Among such anhydrosugar alcohols, isosorbide produced from sorbitol has the widest industrial applicability at present.

Anhydrosugar alcohol can be used in various fields including treatment of heart and blood vessel diseases, medicaments such as patch adhesive, mouthwash, etc., solvents for compositions in the cosmetics industry, emulsifiers in the food industry, etc. In addition, it can increase the glass transition temperature of polymer materials like polyester, PET, polycarbonate, polyurethane, epoxy resin, etc., and improve the strength of such materials. Furthermore, because anhydrosugar alcohol is an environmentally friendly material derived from natural resources, it is very useful in the plastics industry such as bioplastics and the like. It is also known that anhydrosugar alcohol can be used as an adhesive, environmentally friendly plasticizer, biodegradable polymer, and environmentally friendly solvent for water-soluble lacquer.

As such, anhydrosugar alcohol is receiving much interest because of its wide applicability, and the level of practical industrial application thereof is increasing. However, the conventional methods of producing anhydrosugar alcohol have limitations of high cost for the catalyst used in the dehydration reaction, low conversion rate, and low yields of distillation and purification, etc. In addition, in case of crystallization using solvent for anhydrosugar alcohol purification, there is a serious loss of the target product and a large amount of waste is generated, resulting in problems in terms of environment as well as economy.

CONTENTS OF THE INVENTION

Problems to be Solved

To resolve the problems of the prior arts as explained above, the present invention has an object of providing for producing anhydrosugar alcohol by converting hydrogenated sugar (e.g., hexitol) to anhydrosugar alcohol by addition of an acid thereto, distilling the resulting liquid of the conversion reaction and crystallizing the resulting distillate in a solvent, by which the overall yield of anhydrosugar alcohol can be improved, the distillation efficiency can be increased by improving the flowability of the distillate, and the amount of waste and cost for waste disposal can be reduced, resulting in the production of highly pure anhydrosugar alcohol with low cost and high efficiency.

Technical Means

To achieve the above-stated object, the present invention provides a method for producing anhydrosugar alcohol comprising the steps of converting hydrogenated sugar to anhydrosugar alcohol by dehydration reaction; distilling the resulting liquid of the conversion reaction; and crystallizing the resulting distillate in a solvent, wherein the solvent for crystallization is removed from the mother liquor generated from the crystallization step, and the resulting product is fed to the distillation step of the resulting liquid of the conversion reaction, together with a distillate which is not fed to the crystallization step after the distillation step.

Effect of the Invention

According to the present invention, it is possible to improve the overall yield of anhydrosugar alcohol, increase the distillation efficiency by improving the flowability of the distillate, and reduce the amount of waste and cost for waste disposal. Therefore, the method for producing anhydrosugar alcohol of the present invention can be particularly used in mass-production processes on a commercial scale employing distillation and crystallization steps.

BRIEF EXPLANATION OF THE DRAWINGS

FIG. 1 schematically represents a structure of a preferable embodiment of an internal condenser type, thin-film evaporator which can be used in the method for producing anhydrosugar alcohol of the present invention.

CONCRETE EXPLANATION TO CARRY OUT THE INVENTION

The present invention is explained in more detail below.

The method for producing anhydrosugar alcohol of the present invention comprises a step of converting hydrogenated sugar to anhydrosugar alcohol by dehydration reaction.

Hydrogenated sugar, also generally referred to as sugar alcohol, means a compound obtained by adding hydrogen to the reductive end group in sugar. According to the carbon number, hydrogenated sugar is classified into tetritol, pentitol, hexitol and heptitol (4, 5, 6 and 7 carbons, respectively).

Among them, hexitol, having 6 carbons, includes sorbitol, mannitol, iditol, galactitol, etc.—in particular, sorbitol and mannitol are very useful materials.

As used herein, the expression "anhydrosugar alcohol" means any material that is obtained by removing one or more water molecules from the original inner structure of said hydrogenated sugar (or sugar alcohol) in one or more steps by any method.

In the present invention, hexitol is preferably used as the hydrogenated sugar, and more preferably, the hydrogenated sugar for use is selected from sorbitol, mannitol, iditol and mixtures thereof.

Accordingly, in the present invention, dianhydrohexitol—which is the dehydrated product of hexitol—is preferably obtained as the anhydrosugar alcohol, and more preferably, the obtained anhydrosugar alcohol is selected from isosorbide (1,4-3,6-dianhydrosorbitol), isomannide (1,4-3,6-dianhydromannitol), isoidide (1,4-3,6-dianhydroiditol) and mixtures thereof. Among them, isosorbide is particularly useful for industrial and medicinal application.

The hydrogenated sugar is converted to anhydrosugar alcohol by dehydration reaction. There is no special limitation in the method of dehydrating hydrogenated sugar, and any conventionally known method in this field may be utilized as it is or with proper modification.

It is preferable to use an acid catalyst in dehydrating hydrogenated sugar to convert it to anhydrosugar alcohol, and more preferably, acid mixture of a first acid and a second acid can be used. As for the acid catalyst, in the case of a single acid catalyst, sulfuric acid, hydrochloric acid, phosphoric acid, etc. can be used; and in the case of an acid mixture, sulfuric acid can be used as the first acid, and one or more sulfur-containing acids or salts thereof selected from the group consisting of p-toluenesulfonic acid, methanesulfonic acid, ethanesulfonic acid, benzenesulfonic acid, naphthalenesulfonic acid and aluminum sulfate can be used as the second acid. The acid catalyst is preferably used in an amount of from 0.5 to 10 parts by weight per 100 parts by weight of the hydrogenated sugar (e.g., hexitol). If the amount of acid catalyst is much less than the above range, the conversion time to anhydrosugar alcohol may become excessively long. On the other hand, if the amount of acid catalyst is much greater than the above range, sugar polymer may be increasingly generated and the conversion rate may be lowered.

According to an embodiment of the present invention, the step of converting hydrogenated sugar to anhydrosugar alcohol may be conducted in the presence of an acid catalyst as explained above, at a temperature of from 105 to 200° C. (more preferably, 110 to 150° C.) under a pressure of from 1 to 100 mmHg (more preferably, 1 to 50 mmHg) for 1 to 10 hours (more preferably, 2 to 5 hours), but it is not limited thereto.

In the case of using an acid catalyst during the dehydration reaction of hydrogenated sugar, it is preferable to neutralize the reaction product liquid. The neutralization may be conducted after the dehydration reaction by cooling the reaction product liquid (e.g., to 100° C. or lower) and adding thereto conventional alkali such as sodium hydroxide. The neutralized reaction product liquid preferably has a pH of 6 to 8.

According to a preferable embodiment of the method for producing anhydrosugar alcohol of the present invention, the resulting liquid of the step of converting hydrogenated sugar to anhydrosugar alcohol may be pre-treated before being fed to the first distilling step. The purpose of the pre-treatment is to remove moisture and a low-boiling-point substance(s) remaining in the resulting liquid of the converting step, and may be conducted conventionally at a temperature of from 90° C. to 110° C. under a pressure of 10 mmHg to 100 mmHg for 1 hour or longer (e.g., 1 to 4 hours), but it is not limited thereto.

The resulting liquid of the conversion reaction (preferably, the pre-treated resulting liquid as explained above) is then subject to distillation, preferably thin-film distillation.

Preferably, the distillation step is conducted in an internal condenser type, thin-film evaporator comprising an internal condenser, an input line for raw material, an output line for distillation residue, a vacuum line and an output line for distillate.

More preferably, when the distillation using an internal condenser type, thin-film evaporator is conducted, in addition to the depressurization of the inside of the evaporator through the vacuum line it is possible to further depressurize it through the output line for distillation residue.

A structure of a preferable embodiment of an internal condenser type, thin-film evaporator which can be used in the method for producing anhydrosugar alcohol of the present invention is schematically represented in FIG. 1. The internal condenser type, thin-film evaporator 1 according to FIG. 1 comprises internal condenser 5, input line for raw material 6, output line for distillation residue 7, branch line for vacuum formation 7-1, vacuum line 8 and output line for distillate 9, and further comprises heating jacket 2 for heating, wiper 3, condenser guard 4 and cooler input/output lines 10 and 11, respectively. The internal condenser type, thin-film evaporator which can be used in the present invention is not limited to that of the structure shown in FIG. 1, and if necessary, it may further comprise additional components other than the above-explained ones, and the forms thereof may be various.

In a preferable embodiment of the present invention, there is no special limitation in the method of additionally depressurizing the inside of the evaporator through the output line for distillation residue. For example, a vacuum pump connected to the vacuum line can also be connected to the branch line for vacuum formation of the output line for distillation residue, by which the same degree of vacuum can be applied to the output line for distillation residue and the vacuum line. Alternatively, a separate vacuum pump can be connected to the branch line for vacuum formation of the output line for distillation residue, by which an independent degree of vacuum from the vacuum line can be applied to the output line for distillation residue.

The distilling step can be conducted effectively under a temperature condition of preferably from 100° C. to 250° C., more preferably from 100° C. to 200° C., and still more preferably from 110° C. to 170° C. If the distillation temperature is lower than 100° C., the distillation of anhydrosugar alcohol may not be conducted effectively. If the distillation temperature is higher than 250° C., anhydrosugar alcohol may be carbonized or polymer material may be generated, and the color will become dark due to the formation of coloring substance, rendering decolorization difficult Furthermore, anhydrosugar alcohol is thermally decomposed at high temperature and thus byproducts such as formic acid, furfural, etc. are generated, and they lower the purity and pH of the resulting liquid of distillation, which is not industrially preferable.

Under the above preferable temperature condition, the pressure condition (inside the evaporator) of the distilling step is preferably 10 mmHg or less (e.g., 0.0001 to 10 mmHg, more concretely, 0.0001 to 8 mmHg), more preferably 5 mmHg or less (e.g., 0.001 to 5 mmHg), and still more preferably 1 mmHg or less (e.g., 0.01 to 1 mmHg, more concretely 0.01 to 0.8 mmHg). If the distillation pressure is greater than 10 mmHg, the distillation temperature should be elevated in order to distill anhydrosugar alcohol and in such a case, the aforesaid problems may be generated. On the other hand, excessively low distillation pressure is not preferable since an extra cost would be necessitated for a high-vacuum device to lower the distillation pressure and the distillation purity would be lowered.

The distillate obtained as a result of the distilling step is then subject o crystallization using solvent.

As the solvent for the crystallization, for example, one or more organic solvents such as acetone, ethyl acetate, toluene, benzene, xylene, alcohol (e.g., isopropyl alcohol), etc. can be used. According to a preferable embodiment of the present invention, acetone or alcohol (e.g., isopropyl alcohol) is used as the solvent for the crystallization.

There is no special limitation in the method and device for the crystallization, and any method or device which has been known in this field since a long time ago may be utilized as it is or with proper modification. For example, concretely, it is possible to use a method of dissolving the resulting distillate of the distilling step in a solvent such as acetone, ethyl acetate, toluene, benzene, xylene, alcohol, etc. at an elevated temperature if necessary, and then lowering the temperature of the solution to precipitate the anhydrosugar alcohol crystals. The kind and amount of solvent used and the elevated/lowered temperature, etc, may be determined properly according to the processing capacity and concrete facility conditions. According to a preferable embodiment of the present invention, acetone is used as a solvent, and after the solvent and the anhydrosugar alcohol distillate are mixed with a weight ratio of from 10:1 to 1:1, the temperature of the solution is elevated to 30° C. or higher and then lowered to 10° C. or lower to precipitate the anhydrosugar alcohol crystals.

The precipitated anhydrosugar alcohol crystals are separated from the mother liquor by filtration, etc. and if necessary, subject to a subsequent further purification procedure(s).

Meanwhile, in the present invention the solvent for crystallization is removed from the mother liquor generated from the crystallization step.

There is no special limitation in the method and device for removing the solvent from the mother liquor, and any method or device which has been known in this field since a long time ago may be utilized as it is or with proper modification, In addition, there is no special limitation, in the condition for the solvent removal, and in case of using a rotary evaporator, the solvent can be removed by treating the mother liquor at an elevated temperature (e.g., a temperature condition of from 30° C. to 80° C.) under a reduced pressure (e.g., a pressure condition of 250 torr or less) for a proper time (e.g., from 30 minutes to 3 hours). In case of using a thin-film evaporator, continuous removal of solvent is possible.

The purity of anhydrosugar alcohol of the product obtained after the solvent removal is preferably 75% or higher. If the purity is lower than 75%, even though it is fed to the subsequent distillation step, the effect of improving the overall yield may be insufficient.

The product obtained by removing the solvent for crystallization from the mother liquor (also referred to as "the concentrated mother liquor" hereinafter) is fed to the distillation step of the resulting liquid of the conversion reaction, together with a distillate which is not fed to the crystallization step after the distillation step.

The weight ratio of the concentrated mother liquor: distillate, which are fed together to the distillation step, is preferably from 9:1 to 1:9, more preferably from 2:8 to 8:2, and even more preferably from 4:6 to 6:4. When they are fed together to the distillation step, if the amount of the concentrated mother liquor is greater than 9 times the weight of the distillate, the purity of the obtained distillate may be lowered and the efficiency of the subsequent crystallization may decrease. On the contrary, if the amount of the distillate is greater than 9 times the weight of the concentrated mother liquor, the effect of improving yield may be little and the cost may increase.

The amount of the mixture of the concentrated mother liquor and the distillate fed to the distillation step with respect to 100 parts by weight of the resulting liquid of the conversion reaction to be distilled in the same step is preferably from 5 to 50 parts by weight, more preferably from 5 to 40 parts by weight, and even more preferably from 10 to 20 parts by weight. If the amount of the mixture of the concentrated mother liquor and the distillate is less than 5 parts by weight per 100 parts by weight of the resulting liquid of the conversion reaction, the effect of improving yield may be little, and if it is greater than 50 parts by weight, the purity of the obtained distillate may be lowered.

There is no special limitation in the manner of feeding the concentrated mother liquor and the distillate, together with the resulting liquid of the conversion reaction, to the distillation step. For example, before starting the distillation step the concentrated mother liquor, the distillate and the resulting liquid of the conversion reaction may be preliminarily mixed altogether in a separate vessel, and the resulting mixture liquid may then be fed into the evaporator. In an alternative manner, before starting the distillation step the concentrated mother liquor and the distillate may be preliminarily mixed in a separate vessel, and the resulting mixture liquid may then be fed into the line for transferring the resulting liquid of the conversion reaction to the evaporator via a line connected thereto, by which the ingredients are mixed during the transfer and directly fed into the evaporator. In another alternative manner, a line for the concentrated mother liquor and a line for the distillate may independently be connected to the line for transferring the resulting liquid of the conversion reaction to the evaporator, by which the ingredients are mixed during the transfer and directly fed into the evaporator.

The method for producing anhydrosugar alcohol of the present invention may further comprise a step of conducting post-treatment for the anhydrosugar alcohol crystals obtained in the crystallization step, wherein the post-treatment is selected from adsorbent treatment, ion purification, and a combination thereof.

The adsorbent treatment is for decolorization and may be conducted by using a conventional adsorbent such as active carbon according to the conventional method of adsorbent treatment. As the active carbon, one or more selected from active carbon groups obtained by activating plant sources such as wooden material, palm, etc. or mineral sources such as brown coal, bituminous coal, soft coal, anthracite coal, etc. may be used.

The purpose of ion purification is to remove ions that may exist in the anhydrosugar alcohol, and it can be conducted 1 time or more using one or more ion exchange resins selected from strong cationic, weak cationic, strong anionic and weak anionic ion exchange resin groups according to the ion types that may exist.

The present invention is explained in more detail through the following Examples and Comparative Examples. However, the Examples are intended to facilitate understanding of the present invention only, and the scope of the present invention is not limited thereby.

EXAMPLES

Preparation Example 10,000 g of sorbitol powder (D-sorbitol, Samyang Genex Inc.) was fed into a batch reactor equipped with an agitator and melted by heating to 110° C. 100 g of sulfuric acid (Duksan Chemical) and 42 g of methanesulfonic acid (Duksan Chemical) were added thereto, and the reactor was heated to about 140° C. Dehydration reaction was conducted under a reduced pressure condition of about 30 mmHg to convert sorbitol to anhydrosugar alcohol. After the dehydration reaction was completed, the reaction mixture was cooled to 110° C., and about 300 g of 50% sodium hydroxide solution (Samjeon Pure Chemical) was added thereto to neutralize the resulting reaction liquid. The resulting neutralized liquid was set to be at 100° C. and then concentrated under a reduced pressure condition of 40 mmHg or less for 1 hour or longer to remove the moisture and low-boiling-point substance present in the resulting liquid.

Comparative Example 1

The resulting liquid of the conversion reaction obtained in the above Preparation Example was fed into an internal condenser type, thin-film evaporator as shown in FIG. 1, and distilled under conditions of 140° C. of distillation temperature and 5 mmHg of evaporator inside pressure. The purity of anhydrosugar alcohol obtained through the distillation was 98.0%, and the distillation yield was 92%.

1,889 g of the obtained distillate and 940g of acetone were placed in a jacketed equipment for crystallization, and the temperature was elevated to 40° C. and then lowered to 10° C. to generate crystals. This procedure was repeated 3 times. The obtained crystals were filtered and washed with 470 g of acetone to obtain anhydrosugar alcohol crystals with purity of 99.7%. The crystallization yield was 88.0%, and the overall process yield was 62.3%. Gas chromatography (GC, HP) was used to analyze the resulting product.

Example 1

The mother liquor remaining after filtering the crystals in the crystallization step of Comparative Example 1 was collected and placed in a rotary evaporator (Heidloph, Germany), and the temperature was elevated to 50° C. Under vacuum condition of 250 torr or less, acetone Was removed to obtain a concentrated mother liquor. The purity of anhydrosugar alcohol of the concentrated mother liquor was 84%.

540 g of the concentrated mother liquor was mixed with 540 g of a distillate—which was prepared by the same method of Comparative Example 1—and the mixture was then mixed with 7,250 g of the resulting liquid of the conversion reaction prepared by the same method of Preparation Example. The distillation feed prepared as such was distilled in an internal condenser type, thin-film evaporator as shown in FIG. 1 under conditions of 140° C. of distillation temperature and 5 mmHg of evaporator inside pressure. The purity of anhydrosugar alcohol obtained through the distillation was 97.8%, and the distillation yield was 94%.

For the obtained distillate, crystallization was carried out by the same method of Comparative Example 1 to obtain anhydrosugar alcohol crystals with purity of 99.7%. The crystallization yield was 88.0%, and the overall process yield was 67.4%.

Example 2

540 g of the concentrated mother liquor obtained in the same manner as Example 1 was mixed with 810 g of a distillate—which was prepared by the same method of Comparative Example 1—and the mixture was then mixed with 6,980 g of the resulting liquid of the conversion reaction prepared by the same method of Preparation Example. For the distillation feed prepared as such, distillation and crystallization were carried out by the same method of Example 1. The purity of anhydrosugar alcohol obtained through the distillation was 98.2%, and the distillation yield was 94.5%. In addition, the purity of anhydrosugar alcohol after the crystallization was 99.8%, the crystallization yield was 90.3%, and the overall process yield was 69.5%.

Example 3

The resulting liquid of the conversion reaction obtained in Preparation Example was distilled by the same method of Comparative Example 1. For the distillate, crystallization was carried out using isopropyl alcohol, instead of acetone, as a solvent for crystallization. The purity of anhydrosugar alcohol obtained as such was 99.7%, and the crystallization yield was 87.6%.

The mother liquor generated at that time was concentrated in the same manner as Example I to remove isopropyl alcohol and prepare a concentrated mother liquor, and its purity of anhydrosugar alcohol was 84.2%.

The concentrated mother liquor was mixed with the distillate and the resulting liquid of the conversion reaction in the same manner as Example 1, the resulting mixture was then subject to the thin-film distillation in the same manner as Example 1, and for the resulting distillate, crystallization using isopropyl alcohol was carried out. The purity of anhydrosugar alcohol obtained through the distillation was 97.6%, and the distillation yield was 94%. The purity of anhydrosugar alcohol after the crystallization was 99.7%, the crystallization yield was 88.9%, and the overall process yield was 68.1%.

EXPLANATION OF THE SYMBOLS

1: Thin-film evaporator
2: Heating jacket
3: Wiper
4: Condenser guard
5: Internal condenser
6: Input line for raw material
7: Output line for distillation residue
7-1: Branch line for vacuum formation
8: Vacuum line
9: Output line for distillate
10: Cooler input line
11: Cooler output line

The invention claimed is:

1. A method for producing anhydrosugar alcohol with high purity comprising the steps of converting hydrogenated sugar to anhydrosugar alcohol by dehydration reaction; distilling the resulting liquid of the conversion reaction; and crystallizing the resulting distillate in a solvent,
   wherein the solvent for crystallization is removed from the mother liquor generated from the crystallization step, and the resulting product is fed to the distillation step of the resulting liquid of the conversion reaction, together with a distillate which is not fed to the crystallization step after the distillation step.

2. The method for producing anhydrosugar alcohol according to claim 1, wherein the solvent used for the crystallization is one or more selected from acetone, ethyl acetate, toluene, benzene, xylene and alcohol.

3. The method for producing anhydrosugar alcohol according to claim 1, wherein the weight ratio of the product of the solvent removal from the mother liquor distillate, which are fed together to the distillation step, is from 9:1 to 1:9.

4. The method for producing anhydrosugar alcohol according to claim 1, wherein the distillation step is conducted in an internal condenser type, thin-film evaporator comprising an internal condenser, an input line for raw material, an output line for distillation residue, a vacuum line and an output line for distillate.

5. The method for producing anhydrosugar alcohol according to claim 4, wherein when the distillation is conducted, the inside of the evaporator is depressurized by pressure reduction through the vacuum line and additionally through the output line for distillation residue.

6. The method for producing anhydrosugar alcohol according to claim 1, wherein the hydrogenated sugar is hexitol and the anhydrosugar alcohol is dianhydrohexitol.

7. The method for producing anhydrosugar alcohol according to claim 1, wherein an acid catalyst is used in the step of converting hydrogenated sugar to anhydrosugar alcohol by dehydration reaction.

8. The method for producing anhydrosugar alcohol according to claim 1, wherein the resulting liquid of the step of converting hydrogenated sugar to anhydrosugar alcohol is pre-treated to remove moisture and low-boiling-point substance before being fed to the distillation step.

9. The method for producing anhydrosugar alcohol according to claim 1, wherein e distillation is conducted under a temperature condition of from 100 to 250° C.

10. The method for producing anhydrosugar alcohol according to claim 1, wherein the distillation is conducted under a pressure condition of 10 mmHg or less.

11. The method for producing anhydrosugar alcohol according to claim 1 further comprising a step of conducting post-treatment for the anhydrosugar alcohol crystals obtained in the crystallization step, wherein the post-treatment is selected from adsorbent treatment, ion purification, and a combination thereof.

* * * * *